United States Patent [19]

Grollier et al.

[11] Patent Number: 5,227,153
[45] Date of Patent: Jul. 13, 1993

[54] USE OF 4-(2-OXO-3-BORNYLIDENEMETHYL)BENZENESULFPHONIC ACID OR ITS SALTS FOR THE PROTECTION OF HAIR AGAINST ENVIRONMENTAL ATTACKING AGENTS, AND IN PARTICULAR AGAINST LIGHT, AND PROCESS FOR THE PROTECTION OF HAIR USING THIS COMPOUND

[75] Inventors: Jean F. Grollier, Paris; Claude Dubief, Le Chesnay; Chantal Fourcadier, Paris, all of France

[73] Assignee: L'Oreal, Paris, France

[21] Appl. No.: 769,357

[22] Filed: Oct. 1, 1991

Related U.S. Application Data

[63] Continuation of Ser. No. 308,745, Feb. 10, 1989, abandoned.

[30] Foreign Application Priority Data

Feb. 11, 1988 [LU] Luxembourg .............................. 87131

[51] Int. Cl.$^5$ ................................................. A61K 7/44
[52] U.S. Cl. ......................................... 424/45; 424/59; 424/47
[58] Field of Search ......................... 424/71, 45, 59, 47

[56] References Cited

U.S. PATENT DOCUMENTS 4,165,336  8/1979  Boullin et al. ...................... 260/511
4,323,549  4/1982  Boullin et al. ...................... 424/45

Primary Examiner—Nicholas S. Rizzo
Attorney, Agent, or Firm—Cushman, Darby & Cushman

[57] ABSTRACT

Use of 4-(2-oxo-3-bornylidenemethyl)benzenesulphonic acid or its salts for the protection of hair against environmental attacking agents, and in particular against light and process for the protection of hair using this compound.

Use of 4-(2-oxo-3-bornylidenemethyl)benzenesulphonic acid or of its salts to preserve the mechanical properties of hair for degradation by environmental attacking agents, and in particular by light.

The compound is used in proportions of at least 0.3% by weight of free acid, in a cosmetically acceptable, aqueous, alcoholic or aqueous-alcoholic support, and particularly in proportions of 0.4 to 9% by weight.

14 Claims, No Drawings

USE OF 4-(2-OXO-3-BORNYLIDENEMETHYL)BENZENESULFPHONIC ACID OR ITS SALTS FOR THE PROTECTION OF HAIR AGAINST ENVIRONMENTAL ATTACKING AGENTS, AND IN PARTICULAR AGAINST LIGHT, AND PROCESS FOR THE PROTECTION OF HAIR USING THIS COMPOUND

This is a continuation of application Ser. No. 07/308,745 filed Feb. 10, 1989, now abandoned.

Use of 4-(2-oxo-3-bornylidenemethyl)benzenesulphonic acid or its salts for the protection of hair against environmental attacking agents, and in particular against light, and process for the protection of hair using of this compound.

The present invention relates to the use of 4-(2-oxo-3-bornylidenemethyl)benzenesulphonic acid and of tis salts as agents for protecting the keratin in hair against environmental attacking agents, and in particular against light, and to a process for the protection of hair against environmental attacking agents, and in particular against light.

It has been known for a long time that light attacks the keratin in hair. Many publications disclose that natural light destroys some of the amino acids in hair and by changing the capillary fiber causes its mechanical properties to deteriorate; deterioration of the mechanical properties is mainly to be understood as meaning he reduction of the 15% extension level.

The 15% extension level is the weight to be applied to wet hair of given length to extend it by 15%. The higher the weight, the stronger and more elastic the hair.

The use of substances capable of filtering light radiation has already been proposed to combat the attack of the keratin in hair by light. Those tried in particular were filtering agents will-known to the art such as benzophenone derivatives, for example 2-hydroxy-4-methoxybenzophenone and disodium 2,2'-dihydroxy-4,4'-dimethoxy-5.5'-disulphobenzophenone, or dibenzoylmethane derivatives, for example 4-tert-butyl-4'-methoxydibenzoylmethane or p-aminobenzoic acid and its derivatives such as 2-ethylhexyl p-dimethylaminobenzoate, (4'-dimethylaminobenzoyloxyethyl)dimethyl($C_{16}$–$C_{18}$ alkyl)ammonium tosylate (ESCALOL 537 Q), cinnamates such as 2-ethylhexyl p-methoxycinnamate, or 2-phenylbenzimidazole-5-sulphonic acid.

However, these filtering substances did not prove effective for preserving the mechanical properties of hair, namely its elasticity, against the deleterious effects of light.

On the contrary, it has appeared that their presence in some cosmetic compositions could even accentuate the degradation of the mechanical properties, particularly the reduction in the 15% extension level.

The applicants have has now discovered, surprisingly, that 4-(2-oxo-3-bornylidenemethyl)benzenesulphonic acid and its salts can preserve the mechanical properties of hair form degradation by light. It has been possible to reveal this property by exposure in natural light (sunny environment) and artificial light (xenon light emitter in a SUNTEST HANAU type accelerated aging apparatus).

The subject of the present invention is hence the use of 4-(2-oxo-3-bornylidenemethyl)benzenesulphonic acid and its salts as agents for protecting the mechanical properties of hair, and essentially the 15% wet extension level, against degradation caused by environmental attacking agents, and in particular by light.

Salts of the abovementioned sulphonic acid are to be understood as meaning metal salts and more particularly alkali metal, alkaline-earth metal, or the ammonium or amine salts.

According to the present invention, the above-mentioned sulphonic acid or its salts are used for preserving the mechanical properties of hair against attack by light, in quantities at least equal to 0.3% by weight of free acid (before optional neutralization), and preferably between 0.4% and 9% by weight, in a cosmetically acceptable, aqueous, alcoholic or aqueous-alcoholic support. The minimum quantity of 0.3% corresponds to a molar concentration per 100 g of composition of about 0.9 millimole of acid which may be used as free acid or as a salt formed with a metal hydroxide, ammonia or an amine.

The sulphonic acid or its salts according to the invention may be used to protect natural or sensitized hair. "Sensitized hair" is to be understood as meaning hair that has received a permanent wave, dyeing or bleaching treatment.

The cosmetic compositions for hair, used according to the invention, to protect hair against degradation by light and containing 4-(2-oxo-3-bornylidenemethyl)benzenesulphonic acid and its salts as active compound, may be presented as thickened or unthickened aqueous, alcoholic or aqueous-alcoholic solutions (the alcohol usually being a lower alkanol such as ethanol or isopropanol), gels, aerosol foams or sprays and may contain the adjuvants customarily used in compositions for the treatment of hair and suitable for the application under consideration.

These compositions may or may not be followed by rinsing and may form part of shampoos, after-shampoos, rinses to be applied before or after shampooing, before or after dyeing or bleaching, before or after permanent waving or straightening, compositions that are not rinsed off such a s lotions, gels, sprays or foams of setting and blow-drying, lacquers or sprays for holding the style and restructuring compositions.

when the cosmetic compositions used according to the invention form part of compositions whose application is not followed by rinsing the 4-(2-oxo-3-bornylidenemethyl)benzenesulphonic acid or its salts, as active agent preserving the mechanical properties of hair against light, are present in proportions of 0.3 to 5% by weight relative to the total weight of the compositions, and preferably in proportions of 0.4 to 3.5% by weight of free acid.

When the cosmetic compositions used according to the invention form part of composition whose application is followed by rinsing, the acid or its salts are present in proportions of 0.5 to 9% by weight, and preferably 0.5 to 6% by weight of free acid, relative to the total weight of the composition.

The cosmetic compositions for hair according to the invention have a pH between 2 and 9, and preferably between 4 and 8.

The cosmetic compositions used according to the invention may also contain cosmetic agents that are well-known in the art provided they themselves have not adverse effect on the mechanical properties of the keratin in hair.

Adjuvants for cosmetic agents generally present in the cosmetic compositions used according to the invention are, for example, cationic, anionic, amphoteric, non-ionic surface-active agents or mixtures thereof, thickeners, anionic, cationic, non-ionic amphoteric polymers or mixtures thereof, softeners, preservatives, foaming agents, foam stabilisers, electrolytes, pH regulators, anti-fat agents, sequestering agents, perfumes colorings, propellants and organic solvents.

The cationic, anionic, non-ionic, amphoteric surface-active agents or mixtures thereof are generally used in proportion of 0.1 to 50% by weight, and preferably 0.5 to 30% by weight, relative to the total weight of the compositions.

When the cosmetic compositions for hair used according to the invention form part of shampoos, these are essentially characterized in that they contain, besides the above-defined sulphonic acid or its salts, at least one anionic, non-ionic, cationic, amphoteric surface-active agent or a mixture of such surface-active agents, in aqueous medium. The shampoos may also contain various adjuvants such as coloring, preservatives, thickeners, foam stabilisers, synergists, softeners, electrolytes, sequestering agents, one or more cosmetic resins, perfumes, natural essences as well as any other adjuvant customarily used in a shampoo. In these shampoos, the concentration of surface-active agent is generally between 2 and 50% by weight. Their pH is generally between 3 and 9.

When the compositions used according to the invention form part of compositions whose application is not followed by rinsing—lotion, gel, foam, spray or lacquer for blow-drying, setting, styling or treating hair—they generally include, in an aqueous, alcoholic or aqueous-alcoholic medium, besides the above-defined sulphonic acid or its salts, at least one cationic, anionic, non-ionic, amphoteric polymer or a mixture of such polymers, in quantities generally between 0.1 and 10%, and preferably between 0.1 and 3% by weight, and optionally anti-foaming agents.

When the compositions for the treatment of hair according to the invention form part of rinsed lotions, also called "rinses", they are applied before or after dyeing or bleaching, before or after permanent waving, before or after shampooing or between two applications of shampoo, then rinsed after an exposure time.

These compositions may also be aqueous or aqueous-alcoholic solutions optionally containing surface-active agents; they may also e gels. These compositions may also be pressurized as aerosols in the form of sprays of foams.

In these rinsed compositions, the concentration of surface-active agents may vary between 0.1 and 10%, and preferably between 0.5 and 7% by weight. They may also contain non-ionic, cationic, anionic, amphoteric polymers or mixtures thereof.

When the compositions for the treatment of hair are presented as gels, to be rinsed or not, they contain thickeners in the presence or absence of solvents.

The thickeners may be sodium alginate, gum arabic or xanthan gum or cellulose derivatives such as methylcelulose, hydroxymethylcellulose, hydroxyethylcellulose, hydroxypropylcellulose, carboxymethylcellulose or carboxylic polymers such as the "Carbopols". The lotions may also e thickened by mixing polyethylene glycol and polyethylene glycol stearate or distearate or by a mixture of amides and phosphoric esters. The concentration of the thickener may vary from 0.1 to 30%, an preferably 0.2 to 15% by weight, relative to the total weight of the compositions.

It is also possible to use a thickener formed by the ionic interaction of a cationic polymer consisting of a copolymer of cellulose or of a cellulose derivative with a grafted monomeric water-soluble salt of a quaternary ammonium compound (sold under the names "CELQUAT H 100" or "CELQUAT L 200") and of an anionic carboxylic polymer having an absolute capillary viscosity in dimethylforamide or methanol at a concentration of 5% and at 30° C. of not more than $30 \times 10^{-3}$ Pa s.

This thickener is described in Patent Application FR 2,598,611.

When the compositions for the treatment of hair are presented as foams, to be rinsed or not, they contain a foaming agent in aqueous or aqueous-alcoholic medium, in the presence of a propellent gas.

The following maybe used as foaming agents: anionic, non-ionic, cationic, amphoteric surface-active agents or mixtures thereof, non-ionic, anionic, cationic polymers or mixtures thereof, polyvinyl alcohol from the hydrolysis of polyvinyl acetate whose degree of hydrolysis is not more than 97% as described in Patent Application FR 2,598,613.

To produce a foam, it is preferred to use a combination of cationic polymer and anionic polymer, at least one of which foams in aqueous solution. Such combination are described in Patent FR 2,505,348. The propellent gases used to pressurize these compositions destined to form foams are present in proportions not exceeding 25% and preferably 15% relative to the total weight of the composition. The following may be sued as propellent gas: carbon dioxide, nitrogen, nitrogen protoxide, volatile hydrocarbons such as butane, isobutane, propane and mixtures thereof, non-hydrolyable chlorinated and/or fluorinated hydrocarbons such as those sold under the names "FREON" or "DYMEL" by the DU PONT de NEMOURS Company.

When the composition is presented as a spray or lacquer, it contains a film-forming resin in a alcoholic or aqueous-alcoholic medium an optionally in the presence of a propellant gas. As film-forming resin it is preferred to use an anionic polymer containing acrylic or methacrylic acid, crotonic acid or unsaturated $\alpha,\beta$-dicarboxylic acid units.

The propellants used int he lacquer formulations may be selected from among the volatile hydrocarbons such as n-butane, propane, isobutane or mixtures thereof or a mixture of these hydrocarbons with chlorinated and/or fluorinated hydrocarbons such as the compounds sold under the names "FREON" or "DYMEL" by the DU PONT de NEMOURS Company and more particularly the fluorochlorinated hydrocarbons such as monofluorotrichloremethane, diflorodichloromethane, tetrafluorodichloroethane or mixtures of the latter.

They may also be selected from among the above-described chlorinated and/or fluorinated hydrocarbons and mixtures thereof, dimethyl ether, carbon dioxide or nitrous oxide.

The propellent phase, in these lacquer compositions, represents 30 to 80% of the total weight of the pressurized composition.

When the compositions of the invention for the treatment of hair form part of restructuring lotions, they contain products which reinforce the keratin chain in hair. Methylolated derivatives such as those described in French Patents No. 1,527,085 and 1,519,979 belong to this class of products.

The present invention also aims to provide a process for the protection of keratin in hair against environmental attacking agents, and in particular against light, consisting in applying to the hair an effective quantity of 4-(2-oxo-3-bornylidenemethyl)benzenesulphonic acid or of its slats, in cosmetically acceptable, aqueous, alcoholic or aqueous-alcoholic support.

The following examples illustrate the invention without limiting it in any way.

EXAMPLE 1

A hair protecting rinse composition is prepared:

| | |
|---|---|
| 4-(2-Oxo-3-bornylidenemethyl)benzene-sulphonic acid | 5 g |
| Sodium ($C_{12}$–$C_{14}$ alkyl) ether sulphate oxyethylenated with 2.2 moles of ethylene oxide in aqueous solution containing 25% of active substance (AS) | 2 g AS |
| Hydroxyethylcellulose sold by the HERCULES Company under the name "NATROSOL 250 HHR" | 1 g |
| Triethanolamine | qs pH: 7 |
| Coloring, perfume, preservative | qs |
| Water | qs 100 g |

This composition is applied to bleached hair, then rinsed. The hair is then exposed to the Suntest by means of a "SUNTEST HANAU" apparatus for 120 hours. This apparatus consists of a xenon light emitter and a system of filters producing a radiation corresponding to a very large extend to solar radiation. The energy radiation is about 585 W/m² in the wavelength range between 300 and 830 nm (overall radiation).

Treatment with this composition enables the means value of the 15% wet extension level to be very significantly improved compared to hair of the same type treated in an identical way but with a rinse composition containing no 4-(2-oxo-3-bornylidenemethyl)benzenesulphonic acid.

EXAMPLE 2

A hair protecting styling form a of the following composition is prepared:

| | |
|---|---|
| 4-(2-Oxo-3-bornylidenemethyl)benzene-sulphonic acid | 1.5 g |
| Vinyl methyl ether/maleic anhydride copolymer mono-esterified with butanol, sold as a solution in ethanol containing 50% of active substance (AS) by the GENERAL ANILIN Company under the name "GREZ ES 425" | 0.6 g AS |
| Hydroxyethylcellulose grafted with diallyldimethylammonium chloride, sold by the NATIONAL STARCH Company under the name "CELQUAT L 200" | 0.5 g |
| Cationic silicone polymer sold by the UNION CARBIDE Company under the name "UCAR SILICONE ALE 56" as an aqueous solution containing 35% of active substance (AS) | 0.2 g AS |
| Ethyl alcohol | qs: 10° |
| 2-amino-2-methyl-1-propanol | qs pH: 7.5 |
| Perfume, coloring, preservative | qs |
| Water | qs 100 g |

The above composition is packaged in an aerosol device:

| | |
|---|---|
| Composition | 90 g |
| Freons 12/114 (57/43 by weight) | 10 g |
| Total | 100 g |

Freon 12 = difluorodichloromethane
Freon 114 = 1,2-dichlorotetrafluoroethane

After applying this foam to bleached hair three times and without consecutive rinsing, the hair is exposed to the Suntest as described in Example 1 for 180 hours.

Compared to hair of the same type treated in an identical way but with a foam containing no 4-(2-oxo-3-bornylidenemethyl)benzenesulphonic acid, an appreciable improvement in the means value of the 15% wet extension level is observed.

EXAMPLE 3

A hair-protecting styling spray of the following composition is prepared:

| | |
|---|---|
| 4-(2-Oxo-3-bornylidenemethyl)benzene-sulphonic acid | 1 g |
| Crotonic acid/vinyl 4-tert.-butyl benzoate/vinyl acetate terpolymer (10/25/65) prepared according to French Patent No 2,439,798 (Example 19) | 6 g |
| 2-amino-2-methyl-1-propanol | qs for neutralisation |
| Perfume, preservative | qs |
| Ethyl alcohol | qs 100 g |

The above composition is packaged in a pump bottle.

Bleached hair treated with one application of this spray and not rinsed is then exposed to the Suntest under the conditions described in Example 1 for 120 hours. Compared to hair of the same type treated analogously but with a spray containing no 4-(2-oxo-3-bornylidenemethyl)benzenesulphonic acid, a significant improvement in the means value of the 15% wet extension level is recorded.

EXAMPLE 4

A hair-protecting styling gel of the following composition is prepared:

| | |
|---|---|
| 4-(2-Oxo-3-bornylidenemethyl)benzene-sulphonic acid | 0.4 g |
| Crosslinked polyacrylic acid, MW 4 million, sold by the GOODRICH Company under the name "CARBOPOL 940" | 0.5 g |
| 2-amino-2-methyl-1-propanol | qs pH: 7.5 |
| Perfume, coloring, preservative | qs |
| Ethyl alcohol | qs 10° |
| Water | qs 100 g |

Bleached hair treated with one application of this gel and not rinsed is then exposed to the Suntest under the conditions described in Example 1 for 120 hours. Compared to hair of the same type treated analogously but with a gel containing non 4-(2-oxo-3-bornylidenemethyl)benzenesulphonic acid, an appreciable improvement int he means value of the 15% wet extension level is recorded.

EXAMPLE 5

A hair-protecting shampoo of the following composition is prepared:

| | |
|---|---|
| Sodium ($C_{12}$–$C_{14}$ alkyl) ether sulphate oxyethylenated with 2.2 moles of ethylene oxide in aqueous solution containing 25% AS | 3 g AS |

| | |
|---|---|
| Sodium (C₁₄-C₁₅ α-olefin) sulphonate sold in aqueous solution containing 38% AS by the AKZO Company under the name "ELFAN OS46" | 3 g AS |
| Surfactant known as "COCOAMPHOCARBOXY-GLYCINATE" (CTFA 3rd edition 1982), sold under the name "MIRANOL CLM conc." by the MIRANOL Company, in aqueous solution containing 38% AS | 4 g AS |
| Glycoldistearate | 1 g |
| Coconut acid diethanolamide sold under the name "COMPERLAN KD" by the HENKEL Company | 2 g |
| Xanthan gum sold by the KELCO Company under the name "KELTROL T" | 0.6 g |
| 4-(2-Oxo-3-bornylidenemethyl)-benzenesulphonic acid | 1 g |
| Preservative(s), perfume, coloring | qs |
| Water | qs 100 g |
| HCl | qs pH: 5 |

After a few applications of this shampoo, an appreciable improvement in the means value of the 15% wet extension level is recorded.

We claim:

1. A process for preserving the elasticity of hair, as measured by its 15% extension level, from degradation by light, said process comprising applying to said hair, in an amount effective to preserve the elasticity of said hair, a cosmetic composition comprising in a cosmetically acceptable vehicle at least 0.3 percent by weight, calculated as free acid, of 4-(2-oxo-3-bornylidenemethyl) benzenesulphonic acid or a salt thereof, said vehicle being an aqueous, alcoholic or an aqueous-alcoholic medium.

2. The process of claim 1 wherein said 4-(2-oxo-3-bornylidenemethyl) benzene sulphonic acid is present in said cosmetic composition in an amount ranging form 0.4 to 9 percent by weight of free acid, based on the total weight of said compositions.

3. The process of claim 2 wherein the salt of said 4-(2-oxo-3-bornylidenemethyl) benzenesulphonic acid si an alkali metal, alkaline earth metal, ammonium or amine salt thereof.

4. The process of claim 1 wherein said cosmetic composition is in the form of thickened or unthickened aqueous, alcoholic or aqueous-alcoholic solution, a gel, an aerosol foam or a spray.

5. The process of claim 1 wherein said cosmetic composition also includes at lest one cosmetic adjuvant selected from the group consisting of a cationic, anionic, amphoteric or nonionic surfactant or a mixture thereof; a thickener; an anionic, nonionic, amphoteric or cationic polymer or a mixture thereof; a softener; a preservative; a foaming agent; a foam stabilizer; an electrolyte; a pH regulating agent; an anti-fat agent; a sequestering agent; a perfume; a coloring agent; a propellant; and an organic solvent.

6. The process of claim 1 which includes rinsing said hair subsequent to applying said cosmetic composition to said hair, said cosmetic composition comprising said 4-(2-oxo-3-bornylidenemethyl) benzenesulphonic acid or a salt thereof in an amount ranging from 0.5 to 9 percent by weight of free acid based on the total weight of said composition.

7. The process of claim 6 wherein said 4-(2-oxo-3-bornylidenemethyl) benzene sulphonic acid or a salt thereof is present in said cosmetic composition in an amount ranging from 0.5 to 6 percent by weight of free acid based on the total weight of said compositions.

8. The process of claim 1 wherein said cosmetic composition is not rinsed from the hair subsequent to the application of said composition to the hair, said cosmetic composition comprising said 4-(2-oxo-3-bornylidenemethyl) benzenesulphonic acid or a salt thereof in an amount ranging from 0.3 to 5 percent by weight of free acid based on the total weight of said composition.

9. The process of claim 8 wherein sag 4-(2-oxo-3-bornylidenemethyl) benzenesulphonic acid or a salt thereof is present in said cosmetic composition in an amount ranging from 0.4 to 3.5 percent by weight of free acid based on the total weight of said composition.

10. The process of claim 1 wherein said cosmetic composition is in the form of a shampoo, said composition also comprising at least one anionic, nonionic, cationic or amphoteric surfactant, or a mixture thereof, said surfactant being present in an amount ranging from 2 to 50 percent by weight and said vehicle being an aqueous medium.

11. The process of claim 1 wherein said cosmetic composition is in the form of a foam and said vehicle is an aqueous or an aqueous-alcoholic medium, said cosmetic composition also comprising a propellant gas and a foaming agent selected from the group consisting of (1) an anionic, nonionic, cationic or amphoteric surfactant, or a mixture thereof; (2) a nonionic, anionic or cationic polymer, or a mixture thereof; and (3) a polyvinyl alcohol derived from hydrolyzed polyvinyl acetate wherein the degree of hydrolysis is not more that 97%.

12. The process of claim 11 wherein said foaming agent is a combination of a cationic polymer and an anionic polymer, at least one of the said polymers being foaming in water, in the presence of said propellant gas.

13. The process of claim 1 wherein said cosmetic composition is in the form of a spray or lacquer and said vehicle is an alcoholic or aqueous-alcoholic medium, said cosmetic composition also comprising a film-forming resin, said film-forming resin being an anionic polymer containing units of (1) acrylic or methacrylic acid, (2) crotonic acid or (3) an unsaturated α,β-dicarboxylic acid.

14. The process of claim 13 wherein said cosmetic composition also comprises a propellant gas.

* * * * *